(12) United States Patent
Zeleny et al.

(10) Patent No.: US 9,205,971 B2
(45) Date of Patent: Dec. 8, 2015

(54) CARTRIDGE AND METERING DEVICE FOR FLUID-TESTING STRIPS

(71) Applicant: Jabil Circuit, Inc., St. Petersburg, FL (US)

(72) Inventors: Johannes Zeleny, Ortsstrasse (AT); Karl Fuhrmann, Seeufergasse (AT)

(73) Assignee: Jabil Circuit, Inc., St. Petersburg, FL (US)

( * ) Notice: Subject to any disclaimer, the term of this patent is extended or adjusted under 35 U.S.C. 154(b) by 135 days.

(21) Appl. No.: 13/655,154

(22) Filed: Oct. 18, 2012

(65) Prior Publication Data
US 2013/0098939 A1    Apr. 25, 2013

Related U.S. Application Data

(60) Provisional application No. 61/549,382, filed on Oct. 20, 2011.

(51) Int. Cl.
| | |
|---|---|
| *B65D 83/08* | (2006.01) |
| *B01L 3/00* | (2006.01) |
| *G01N 33/487* | (2006.01) |
| *B01L 9/00* | (2006.01) |
| *G01N 35/00* | (2006.01) |

(52) U.S. Cl.
CPC .............. *B65D 83/0829* (2013.01); *B01L 3/00* (2013.01); *B01L 9/52* (2013.01); *G01N 33/48757* (2013.01); *G01N 35/00* (2013.01); *B01L 2200/04* (2013.01); *B01L 2200/0689* (2013.01); *B01L 2300/0825* (2013.01); *B01L 2300/123* (2013.01); *G01N 2035/00089* (2013.01); *G01N 2035/00108* (2013.01)

(58) Field of Classification Search
CPC .................. A61B 10/0045; A61B 2562/0295; A61B 5/1411; A61B 5/14546; G01N 2001/028; G01N 2035/00019; G01N 33/48757; G01N 33/48764; G01N 33/48771; G01N 33/48778; G01N 33/523
USPC ........................................................ 422/401
See application file for complete search history.

(56) References Cited

U.S. PATENT DOCUMENTS

| 4,911,344 A | 3/1990 | Kahler |
| 6,176,119 B1 | 1/2001 | Kintzig |
| 6,514,769 B2 | 2/2003 | Lee |

(Continued)

FOREIGN PATENT DOCUMENTS

| CN | 1377300 A | 10/2002 |
| CN | 1876519 A | 12/2006 |

(Continued)

OTHER PUBLICATIONS

International Preliminary Report on Patentability issued on PCT/US2012/060857, report issued Apr. 22, 2014.

(Continued)

*Primary Examiner* — Sally Merkling
(74) *Attorney, Agent, or Firm* — Volpe and Koenig, P.C.

(57) ABSTRACT

A cartridge for holding and ejecting fluid test strips and a test-strip metering device for use with such a cartridge. The cartridge holds the test strips in a sheet-like configuration. The metering device is able to extract test strips from the cartridge in response to an actuation of a single user-interface element. The metering device may test the fluids as each is extracted.

15 Claims, 12 Drawing Sheets

(56) References Cited

U.S. PATENT DOCUMENTS

| | | |
|---|---|---|
| 6,534,017 B1* | 3/2003 | Bottwein et al. ............... 422/561 |
| 7,337,918 B2 | 3/2008 | Fowler et al. |
| 2003/0116583 A1 | 6/2003 | Pugh |
| 2003/0191415 A1 | 10/2003 | Moerman et al. |
| 2007/0293790 A1 | 12/2007 | Bainczyk et al. |
| 2008/0034834 A1 | 2/2008 | Schell |
| 2008/0164280 A1 | 7/2008 | Kuriger et al. |
| 2008/0181818 A1 | 7/2008 | Ruan |
| 2008/0217353 A1 | 9/2008 | Newman et al. |
| 2008/0217354 A1 | 9/2008 | Newman et al. |
| 2009/0008395 A1 | 1/2009 | Sattler |
| 2010/0072270 A1 | 3/2010 | Creaven et al. |
| 2010/0317935 A1* | 12/2010 | Roe et al. ...................... 600/309 |

FOREIGN PATENT DOCUMENTS

| | | |
|---|---|---|
| CN | 101266240 A | 9/2008 |
| EP | 1531934 A2 | 5/2005 |
| WO | 2010139864 A1 | 12/2010 |
| WO | WO-2010/139864 | 12/2010 |

OTHER PUBLICATIONS

International Search Report and Written Opinion issued on PCT/US2012/060857, mailed Mar. 29, 2013.

* cited by examiner

CARTRIDGE AND METERING DEVICE FOR FLUID-TESTING STRIPS

This application claims priority to U.S. Provisional Application No. 61/549,382 filed on Oct. 20, 2011, which is hereby incorporated by reference in its entirety as if fully set forth herein.

BACKGROUND

Various medical conditions and treatments require the occasional testing of body fluids, such as blood, in order to monitor general health and effects of treatment. Additionally, fluids may be tested for non-medical reasons, such as blood-alcohol testing in law enforcement. Several devices are currently available on the market for measuring aspects of body fluids, including devices that use electrochemical or photometric techniques, among other example techniques. In electrochemical analyses, input electrical signals are typically applied to fluids and resulting electrical signals are measured. In photometric testing, light signals are applied to fluids and resulting light signals are measured. Other testing such as wet chemical analysis, mass spectrometry, or droplet evaporation analysis may also be used to test fluids.

SUMMARY

A problem recognized by the present inventors in currently available fluid-testing systems is that they are bulky, difficult to use, and indiscreet. Additionally, fluid test strips in presently available systems are not effectively protected against contamination by dust, bacteria, fluid on adjacent test strips, and/or other particles.

In one embodiment, an example cartridge for test strips includes a support structure and a thin-walled housing encompassing the support structure. The support structure is configured to hold several test strips in a sheet-like array. The cartridge may be thin and may include mechanisms for dispensing test strips and sealing the test strips against contamination.

In another embodiment, an example metering device is configured to accommodate a thin, flat test strip holder and dispenser. The metering device includes an interface element (e.g., a button or switch) that allows a user to dispense test strips from the cartridge. The metering device may also include systems for testing the fluids on the test strips, and displaying results of the testing. In some implementations, a single interaction with the interface element may cause the metering device to trigger the test-strip dispensing, fluid metering, and displaying of results.

The foregoing is a summary and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined by the claims, will become apparent in the detailed description set forth herein and taken in conjunction with the accompanying drawings.

DETAILED DESCRIPTION

I. Example Cartridge Architecture

Figure 1:
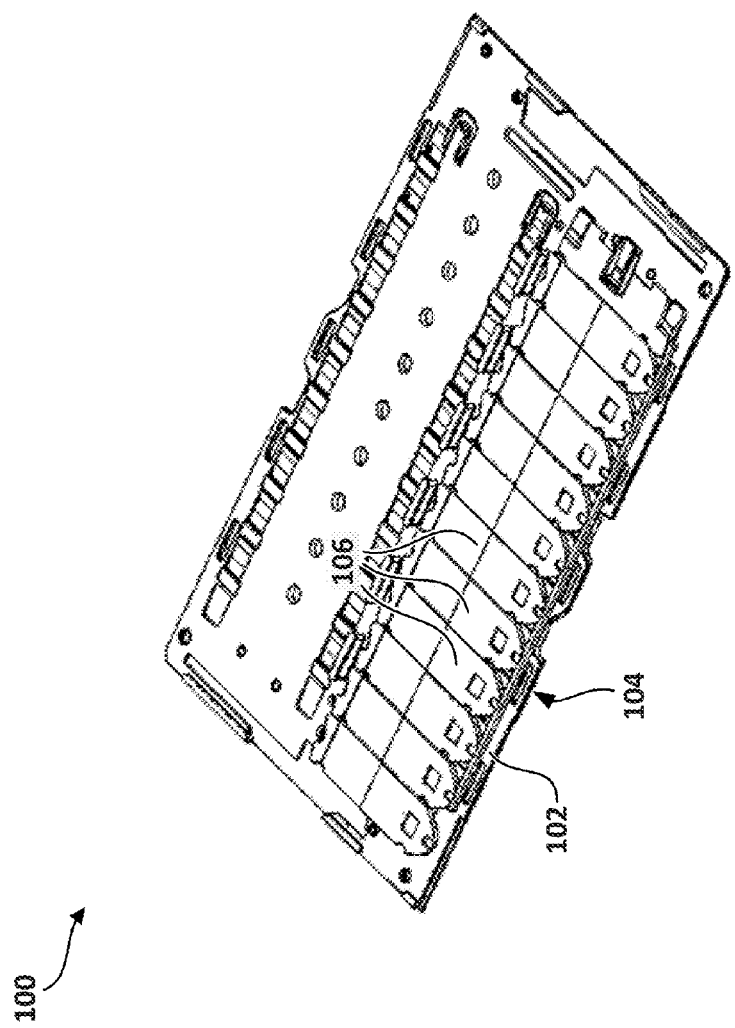
FIG. 1 shows an example cartridge holding an example array of test strips.

FIGS. 1-4 illustrate example cartridge architectures. FIG. 1 shows an internal view of an example cartridge 100. As shown, cartridge 100 includes support structure 102 that holds array 104 of test strips (e.g., test strips 106). As shown, test strips 106 may be relatively flat, each having length and width that is much larger than the depth of each test strip. In array 104, the test strips are laid with a thin side of each strip adjacent to a thin side of a neighboring strip (i.e., side-by-side rather than stacked on top of each other). In this way, array 104 is a thin, flat configuration that is sheet-like (i.e., thin and flat like a sheet of paper) in dimension. Although the particular arrangement shown in FIG. 1 has the longer sides of each test strip placed directly adjacent to each other, other arrangements may place the test strips side-by-side in different ways.

In some cases, support structure 102 that holds array 104 may simply be an open channel in the housing into which test strips may be laid. Additionally, support structure 102 may include spring elements to hold the test strips in place to avoid disarrangement caused by the any open space in array 104.

Figure 2:
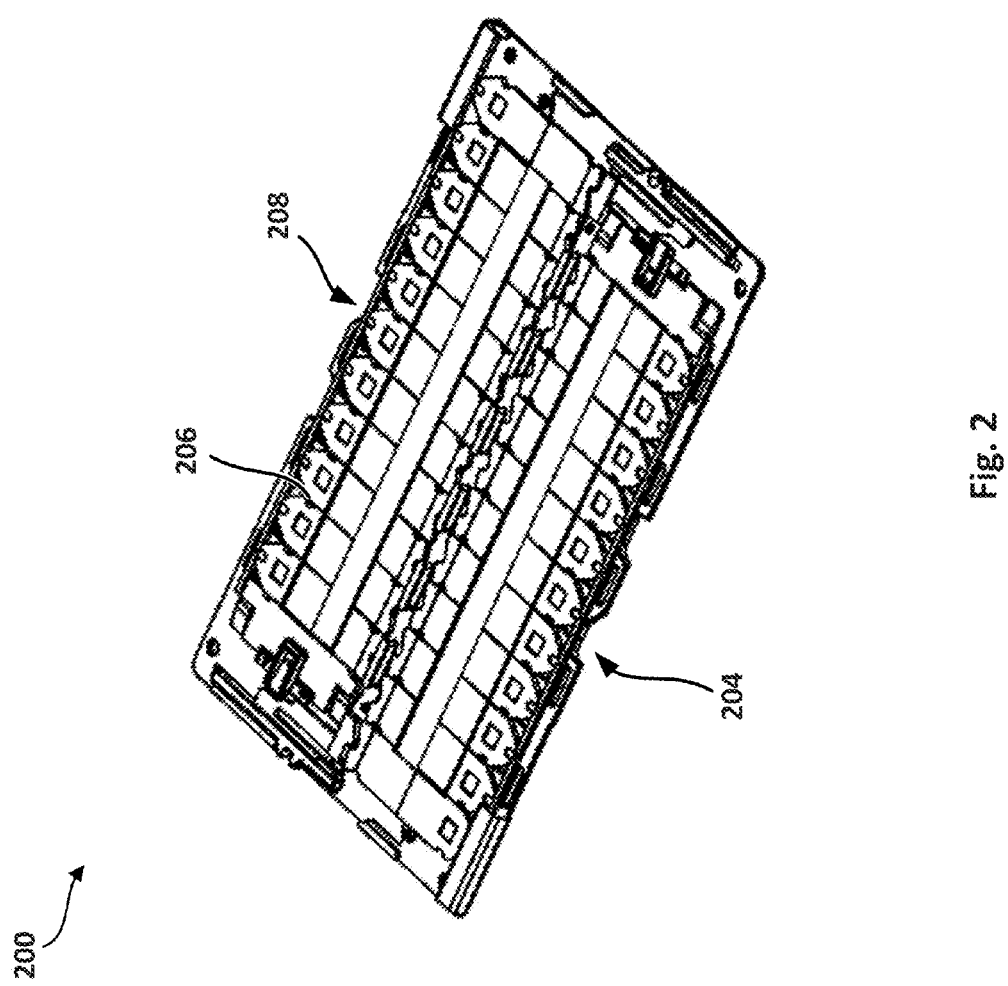
FIG. 2 shows an example cartridge holding multiple arrays of test strips.

FIG. 1 shows a particular number of test strips in array 104. However, this number of test strips is not essential and can vary according to the size of the cartridge, size of the metering device, and/or size of the test strips. For example, a handheld cartridge may contain at least one array of 10-15 test strips. As another example, FIG. 2 shows a cartridge 200 that includes a second support structure 206 to support a second array of test strips 208, thereby holding 20-30 test strips. Other embodiments may support greater than two arrays of test strips or may support arrays of greater than 15 test strips. As shown in FIG. 2, the second array of test strips 208 has roughly the same elements as first array 204, but second array 208 is oriented facing the opposite direction as first array 204. In particular, if first array 204 were turned 180° around the geometric center of cartridge 200, then all the elements of the turned first array would be in the same position as corresponding elements in second array 208. In other embodiments, the second array of test strips may be oriented in other ways with respect to the first array of test strips. Further, in some embodiments, each of the arrays may have different features and/or different numbers of test strips.

With a common size for test strips, the layout of cartridge 200 may result in about a credit-card-sized cartridge, making the cartridge convenient for pocketing.

Figure 3:
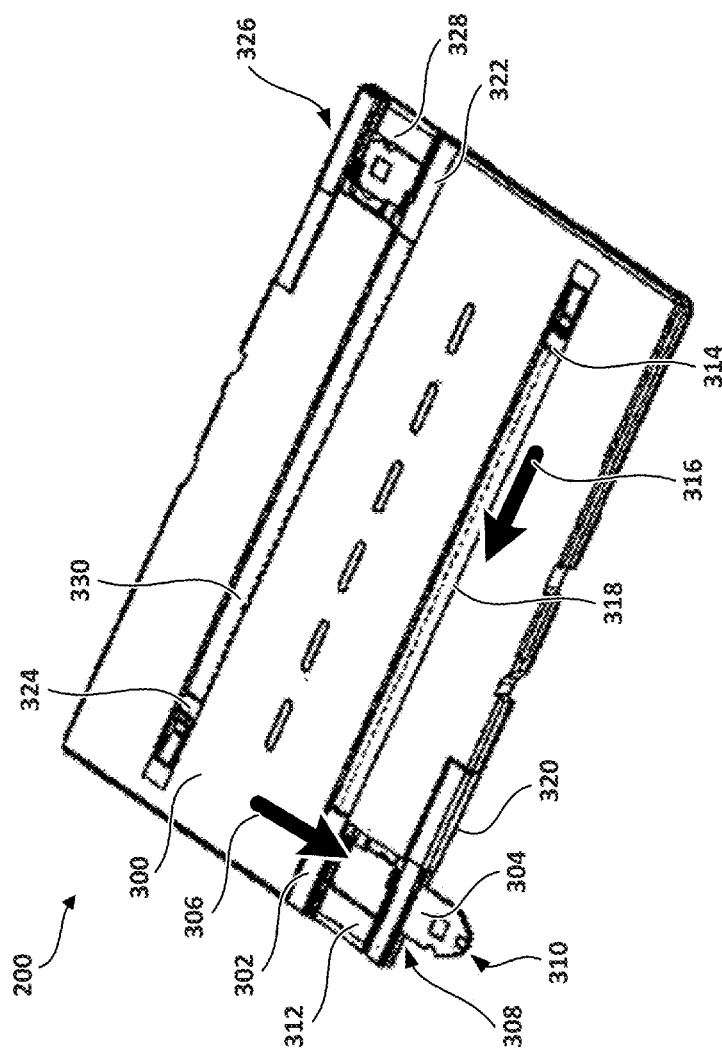
FIG. 3 shows an external view of the underside of an example cartridge in the process of dispensing a test strip.

In addition to holding test strips, a cartridge may include mechanisms for moving and dispensing the test strips. FIG. 3 shows elements that facilitate movement of array of test strips 204 held in cartridge 200. In particular, FIG. 3 is an underside view of cartridge 200, showing housing 300 along with other elements that are accessible from the underside of cartridge 200. As shown, cartridge 200 includes an "ejector" 302 that, when actuated, applies pressure to test strip 304 in order to push test strip 304 at least partially through opening 308 in the direction indicated by arrow 306. With test strip 304 in this position, the contacts of the electrical connectors from the metering device may interface with test strip 304 either on a portion of test strip 304 that has been pushed through opening 308 or on a portion exposed by opening 312. In some cases, the electrical connectors may interface with electrical contacts on the test strip. In other cases, the connectors may interface with a portion of the test strip that carries fluid. In either case, the electrical conductor may apply electrical signals to the captured fluids.

Although not particularly shown, the ejector may include features that can be caught, latched, pushed, pulled, held, actuated, or otherwise engaged to cause the ejector to dispense test strip 304. Such features may include, for example, grooves, indentations, holes, ridges, hooks, handles, buttons, teeth, knife-edges, among other examples. These features may be continuous across the underside or localized to certain areas. These features may be accessible through opening 312.

In order to facilitate capturing fluids, test strips may include a capillary tube 310 that is operable to receive and convey the fluids to the electrical contact regions or to another area of measurement. In some cases, the capillary tube may include a sharpened end so that blood or other internal fluids may be received directly into the test strip. When test strip 304 is in the position shown in FIG. 3, fluids may be extracted and received into capillary tube 310 and electrical connectors may be connected to the fluid for testing.

Test strip 304 may then be removed from cartridge 200 through opening 308. Once test strip 304 is removed through opening 308, the next test strip in line may be moved into the vacancy left by test strip 304. In order to facilitate this movement, a slider 314 may be provided below the test strips so that array 204 may be moved together into a new position after test strip 304 is removed from cartridge 200. As shown, the tests-strips may move in the direction indicated by arrow 316 (called the transport direction) which is towards opening 308.

This slider may also include hooks or barbs in order to prevent the test strips from moving in the direction opposite transport direction. On the underside of the cartridge, the slider may also include features like those of the ejector that can be engaged by a user to move the slider from the outside of the cartridge.

As also shown in FIG. 3, cartridge 200 may include elements for interacting with second array of test strips 208. In particular, cartridge 200 may include ejector 322, slider 324 and openings 326 and 328 that may function the same as the corresponding elements that interact with array 204.

In addition to openings 308 and 312, FIG. 3 shows openings 318 and 330 for movement and interfacing with slider 314. When used without a metering device, a user may actuate the slider and ejector by, for example, sliding their finger across the features exposed by openings 312, 318, 328, and 330. In order to ensure protection against dust, water vapor, and other contaminants, the cartridge includes sealing structures that prevent ambient air from entering the cartridge. In particular, to keep air from entering through openings 312 and 328, gaps between housing 300 and each of ejectors 302 and 322 may be sealed. To keep air from entering through openings 318 and 330, gaps between housing 300 and sliders 314 and 324 may also be sealed. Further, opening 308 may be sealed when not in use. Sealing structures may include labyrinth seals, elastomeric seals, and adhesive foil seals, among other examples. In the case of adhesive foils seals, moving parts may be provisioned with specific features (e.g., glide ribs) to be movable across the adhesive surface without sticking.

To seal some openings (e.g., openings 308 and 326), a cartridge may include one or more sliding seals that may seal and unseal in response to actuation. For example, metal sliding seal 320 may open when ejector 302 pushes a test strip through opening 308. When no test strip is being pushed through opening 308, metal sliding seal 320 may be moved back in front of opening 308, sealing the opening. Such a sliding seal may also include any of the particular sealing structures described above, such as labyrinth, elastomeric or other sealing structures.

Figure 4:
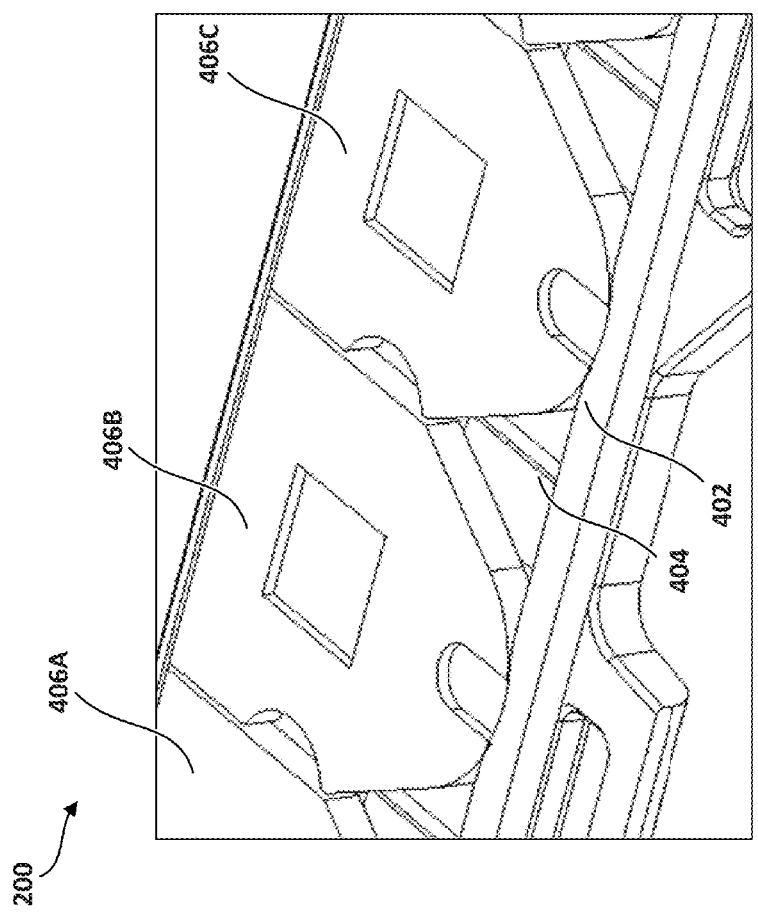
FIG. 4 shows an example array of test strips interfacing with an elastomeric seal.

In addition to sealing the housing of the cartridge, the individual test strips may also be sealed against contamination. As shown in FIG. 4, a cartridge may include elastomeric layer 402 inside the first support structure 404 so that the capillary tube of each test strip (406A, 406B, and 406C) may be pressed into elastomeric layer 402. Elastomeric 402 may deform to accommodate the capillary tube of each test strip. In this way, any contamination that does enter the cartridge is kept out of the fluid test strip. The squeeze force of elastomeric layer 402 on test strips 406 may be partially equalized when the test strips move due to a sloped geometry of the rear supporting-wall in the cartridge.

Figure 5:
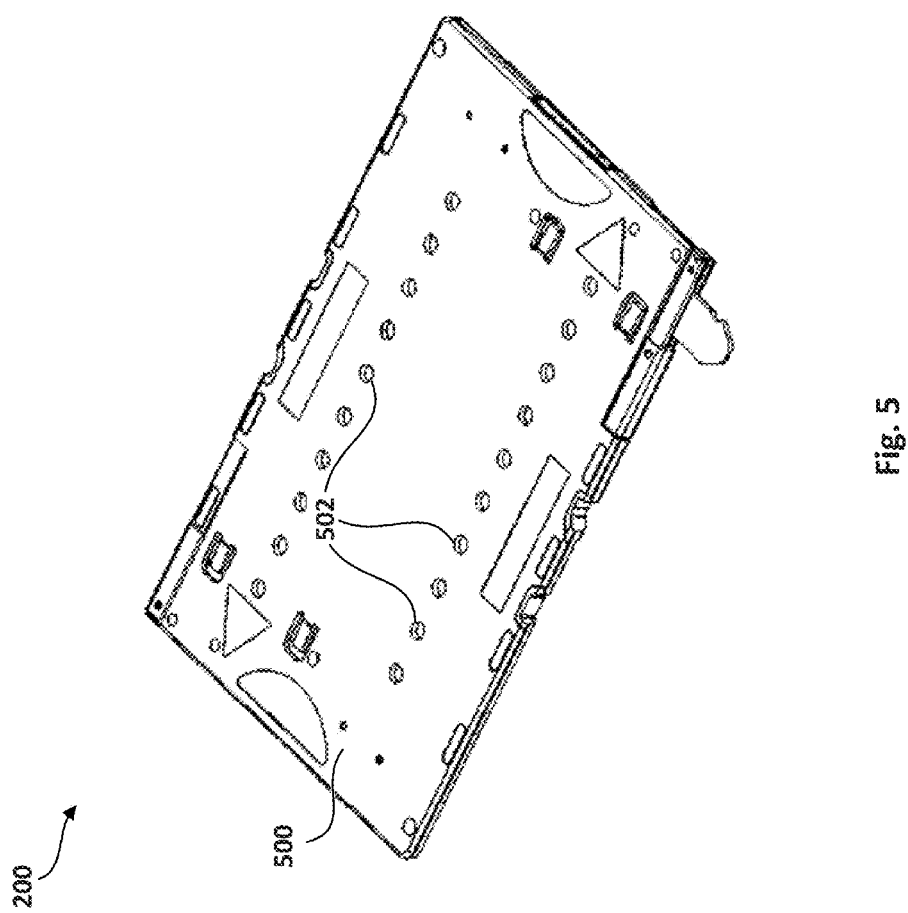
FIG. 5 shows an example top housing of a cartridge.

FIG. 5 shows the top housing 500 of cartridge 200. As shown, top housing 500 may include viewing windows 502 to allow a user to visually check the status of the cartridge (e.g., how many test strips remain, whether the test strips are functional). In some cases, viewing windows may be designed so that a particular part of the test strip may be seen through the windows. In some embodiments, the test strips may be given marks along the portion of the test strips that is visible through the viewing windows. For example, a test strip may have a mark that changes color when fluid has been applied to the test strip. In still other embodiments, top housing 500 of cartridge 200 may be formed substantially out of a transparent material, so that test strips maybe visible without the need for windows 502.

II. Metering Device

FIGS. 6-11 illustrate aspects of an example metering device that may be used with the above-described test-strip cartridge. In some cases, the metering device may be designed to function only with the above-described cartridge. In other cases, the metering device may be configured to accommodate a variety of cartridges.

Figure 6:
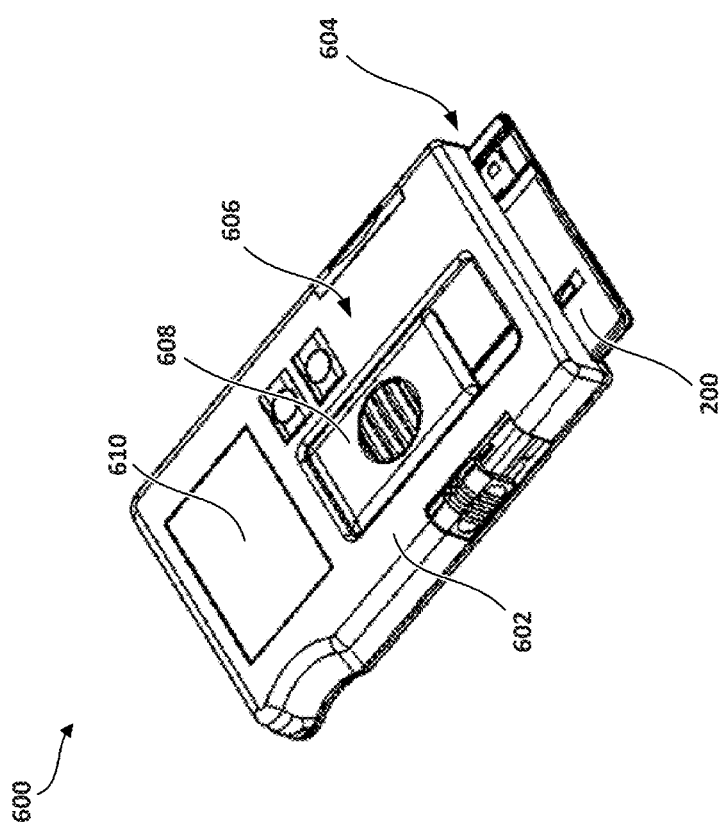
FIG. 6 shows an example metering device receiving a cartridge.

As shown in FIG. 6, metering device 600 may be designed to receive cartridge 200 into a cartridge bay 604. FIG. 6 shows cartridge 200 protruding from cartridge bay 604. An example embodiment, though, may receive cartridge fully into cartridge bay 604. In some embodiments, cartridge bay 604 may include spring elements and locking elements for receiving cartridge 200 and holding cartridge 200 fixed. In such an embodiment, cartridge bay 604 may also use the spring elements to eject cartridge 200.

Also as shown in FIG. 6, metering device 600 may include housing 602 and interface elements 606 for receiving user-input. In particular, interface elements 606 include a button that may be actuated to trigger internal mechanisms.

Although referred to as "user-input" such a triggering may occur in response to a variety of input techniques. For example, metering device 600 may respond to the actuation of button 608 in the same way regardless of whether a human, automated, or natural entity provides the force to actuate button 608. Other examples are also possible. In addition to an implementation with a single button 608, other embodiments may include a variety of separate interface elements 606 to control particular functions of the metering device.

Further, as shown in FIG. 6, metering device 600 may include display 610 for outputting the results of testing. Display 610 may include any standard display type (e.g., light-emitting diode array, liquid crystal display, etc.) Results of testing may be displayed as numbers, symbols, words, or other indicia and may the displayed results may describe various features of the tested liquid. For example, if the metering device tests for blood-glucose levels, the result may be a numerical representation of the concentration of glucose in the blood. Alternatively, the result may include other information, such as the units of concentration, whether the reported concentration is below a certain threshold level, etc. As another example, if the test is for concentration of alcohol in saliva, the result may be a numerical concentration result or a simple indication of whether the concentration is above or below a predefined concentration. In addition to results, display 610 may also indicate other information. For example, while the fluid on a test strip is being measured, display 610 may indicate that measurement is still under way, so that a user does not attempt to test the next strip prematurely.

Figure 7:
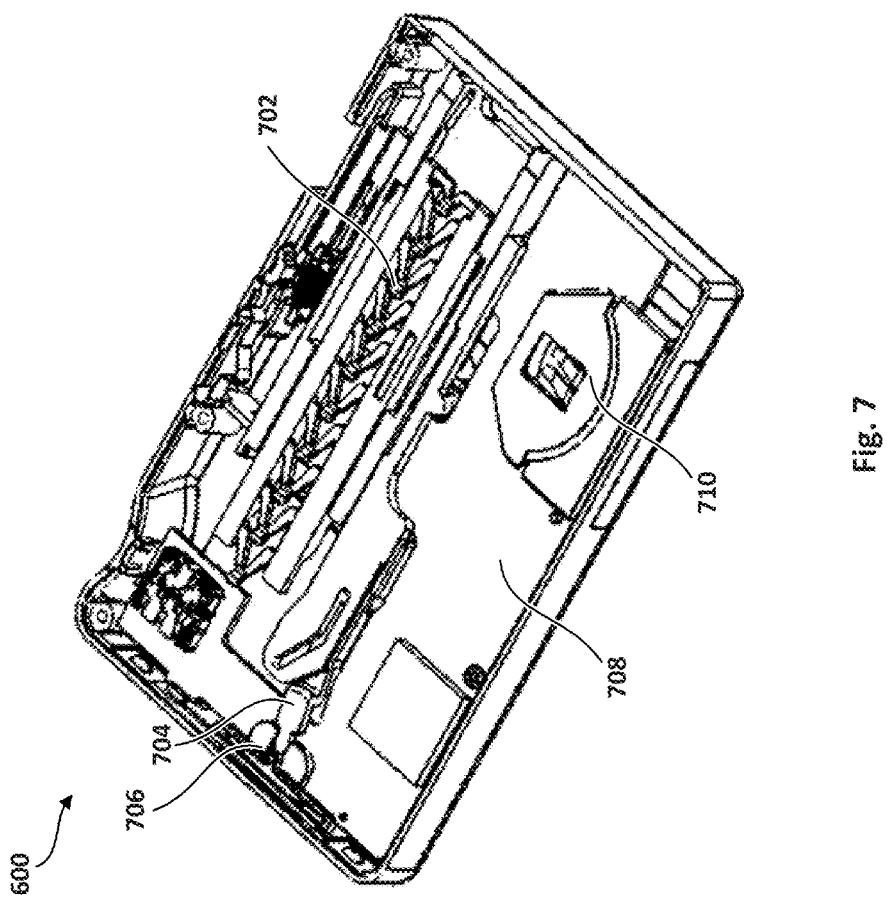
FIG. 7 shows an example toothed gear-rack.

FIG. 7 shows internal features of metering device 600, including a toothed gear-rack 702, a sliding lever 704 attached to a movable nut 706, metering and other electronics 708, and a battery 710. As will be explained, these and other elements may cause the movement, ejection, and measurement of test strips that are initially within an inserted cartridge.

Figure 8:
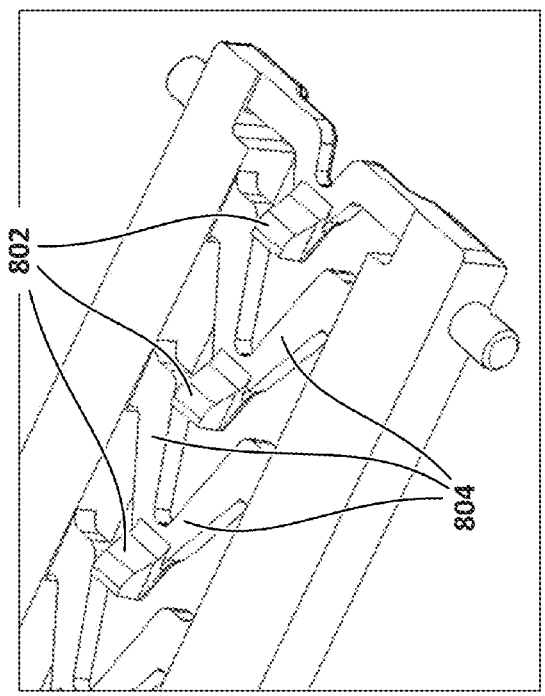
FIG. 8 shows internal mechanisms of an example metering device.
Figure 9:
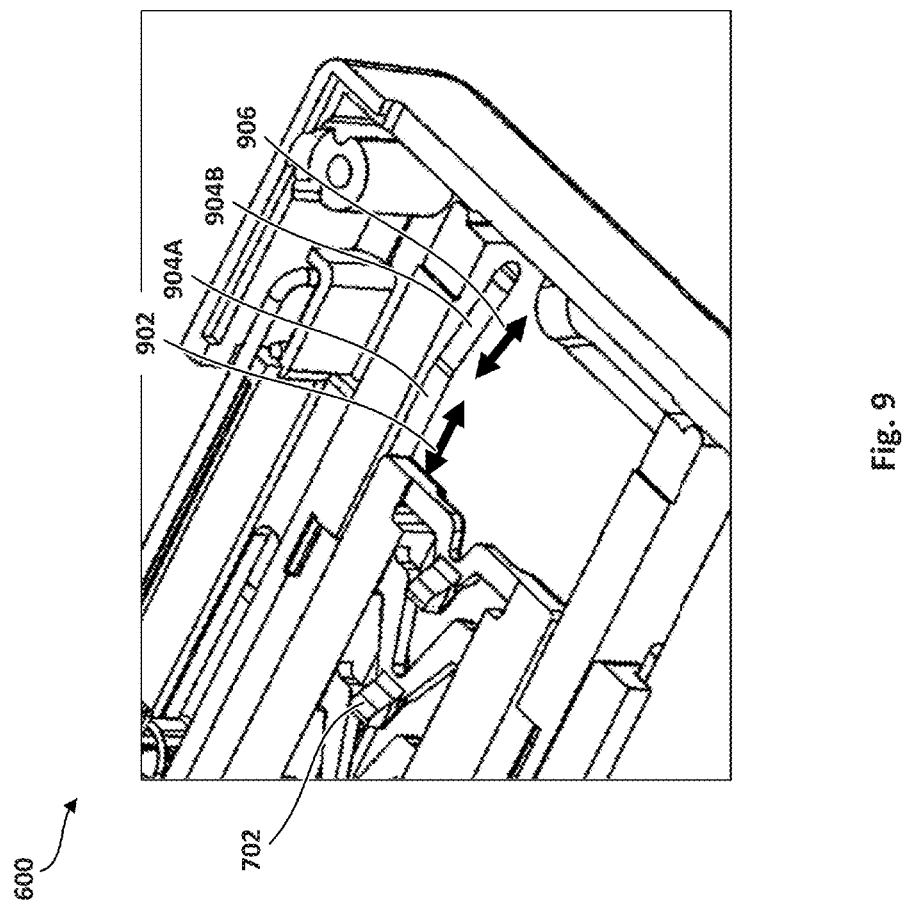
FIG. 9 shows internal mechanisms of an example metering device.

FIG. 8 shows a magnified image of toothed gear-rack 702. As shown, the gear rack includes a set of ramp-shaped teeth 802, each tooth attached to a spring-element 804. FIG. 9 shows toothed gear-rack 702 in place in metering device 600. In metering device 600, gear-rack 702 may connect directly to button 608 so that, as button 608 is actuated by user-input, gear-rack 702 is also actuated. As shown by movement arrow 902, gear-rack 702 may initially slide up ramping surface 904A of an underlying support structure. Then, as shown by movement arrow 906, gear-rack 702 may slide along flat surface 904B of the underlying support structure until button 608 reaches its maximum displacement. Then, gear-rack 902 may slide back across flat surface 904B and down surface 904A in connection with button 608 moving back to its initial position.

If cartridge 200 is held in cartridge bay 604, then the motion of gear-rack 702 may cause the slider in the cartridge 200 to move array of test strips 204 towards opening 308. In particular, teeth 802 may engage with the features on the underside of slider 314 through opening 412. When button 608 is in its initial position, gear-rack 702 may be sufficiently below cartridge 200 that teeth 802 are not engaged with slider 314. In such a situation, cartridge 200 may be removed from metering device 600. As gear-rack 702 moves up ramped surface 904A, teeth 802 may come in contact with and engage slider 314. Then, as gear-rack 702 moves across flat surface 904B, the engaged teeth 802 may push slider 314, along with array 204, towards opening 308. As button 608 and gear-rack 702 move back to their initial positions, teeth 802 may disengage with slider 314 because of their ramped shape and because of the bending of spring elements 804. As gear-rack 702 moves back down ramped surface 904A, teeth 802 may move away from cartridge 200 until fully disengaged from slider 314.

Various considerations may be taken into account in designing the interface element and gear-rack system. For example, the length of the track on which button 608 moves (i.e., the maximum distance that button 608 may move) may be selected, based on the size of the test strips, to ensure that array 204 only moves the width of one test strip when button 608 is actuated. Additionally, the strength of the spring elements used in the movable mechanisms may be chosen to minimize the force necessary for actuation of button 608.

Figure 10:
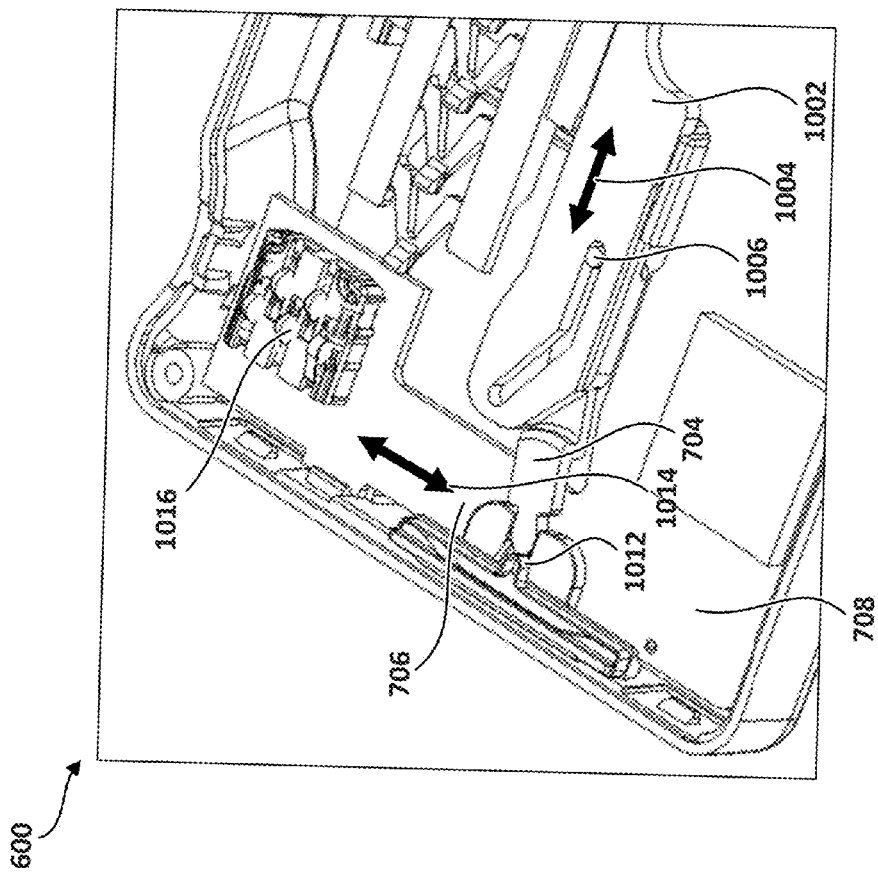
FIG. 10 shows internal mechanisms of an example metering device.

In addition to moving gear-rack 702, actuation of button 608 may move sliding lever 904. To illustrate, FIG. 10 shows a magnified view of lever 904 with the surrounding parts of metering device 600. When button 608 is actuated, slotted link 1002 also moves along the direction indicated by arrow 1004. This link may be part of gear-rack 702 or a separate piece that connects to the same interface element. Sliding lever 904 connects to slotted link 1002 by pin 1006, which impinges through the slot in slotted link 1002.

For the first half of slotted link 904's forward movement, pin 1006 may be pushed in a downward direction (i.e., the direction away from gear-rack 702) due to the shape of sliding link 1002's slot. In turn, this force on pin 1006 may push lever 904 in an opposite direction along the direction indicated by arrow 1014. This lever actuates a movable nut 706, which includes a cam 1012 that may either engage or disengage with ejector 302 of cartridge 200 depending on the direction that cam 1012 is moving. In particular, when cam 1012 is moving upward (towards gear-rack 702), the cam does not engage with ejector 302. And, when cam 1012 is moving downward, the cam engages with ejector 302. Hence, during the first half of the forward movement of sliding link 1002, the cam moves into place under ejector 302 without causing ejection.

For the second half of the forward movement and the first half of the backward movement, the slot may move along pin 1006 without affecting lever 904 because of the shape of the slot. Then, during the second half of the backward movement of sliding link 1002, cam 1012 engages with ejector 302 to cause cartridge 200 to eject a test strip. Cam 1012 is located on a spring feature that allows engagement and disengagement with the ejector 302 at a certain force. When combined with the movement of gear-rack 702, the effect of a single stroke of button 608 is that a test strip is pushed into a dispensing position and is then dispensed into a measuring position. In some cases, the dispensing step may cause the test strip to be completely ejected from the cartridge, thereby freeing up the dispensing position for the next actuation of button 608. In other cases, a separate process may be used to remove a partially ejected test strip from the cartridge.

Although FIGS. 8-10 show a particular way that each part may be moved to cause the movement and ejection of test strips, other example implementations may be used. For example, if a cartridge is designed so that a user must push the ejector 302 in a different direction to eject a test strip, then lever 904 may be positioned to move in the necessary direction. As another example, ramp-shaped teeth 802 may be turned in the opposite direction to cause a movement of array 204 in the opposite direction. In such an embodiment, teeth 802 would not engage with the slider until the backward movement and the teeth would push the array away from opening 308. Other examples of variations are possible.

Additionally, in some cases, gear-rack 702 and sliding link 1002 may not be physically connected to button 608. Rather, the actuation of button 608 may activate an electronic system that uses electrical motor, servos, or actuators to move gear-rack 702 and sliding link 1002. In this way, a user may supply only the force needed to activate the system, instead of supplying the mechanical force by actuating button 608.

Once ejected, the test strip may be measured using fluid contacts 1016 and electronics 708. In particular, electronics 708 may provide electrical input signals to contacts 1016 and/or receive measurement signals from contacts 1016 to test the properties of fluids on the ejected test strip. Contacts 1016 may include electrical contacts for electrochemical analysis, such as a multi-pole connector to make electrical contact with the fluid on a test strip and relay signals to metering electronics in electronics 708. Electronics 708 may include circuits and systems for measuring, processing of results, displaying results, and/or communicate the data to a separate system. Battery 708 provides the necessary power to run the functions of electronics 708. In some embodiments, contacts 1016 may include other types of interfaces for testing fluids. For example, contacts 1016 may include photometric sensors, enzyme analyzers, or DNA testing systems, among other examples. For measuring and processing results, electronics 708 and contacts 1016 may use any of the currently available methods for testing fluids, or any technique that will be made available hereafter.

Metering device 600 can also include a secondary ejector for removing the test strip from the measuring position after the measurement is finished. Such an ejector may discard the test strip either through an output opening in the metering device or into an area of metering device 600 that is designated for used test strips. In this way, the measurement area may be vacated in preparation for the next test strip. The secondary ejector may eject the measured test strip in response to the measurement electronics completing measurement. In other cases, the secondary ejector may activate along with the other mechanical elements when button 608 is actuated.

Figure 11:
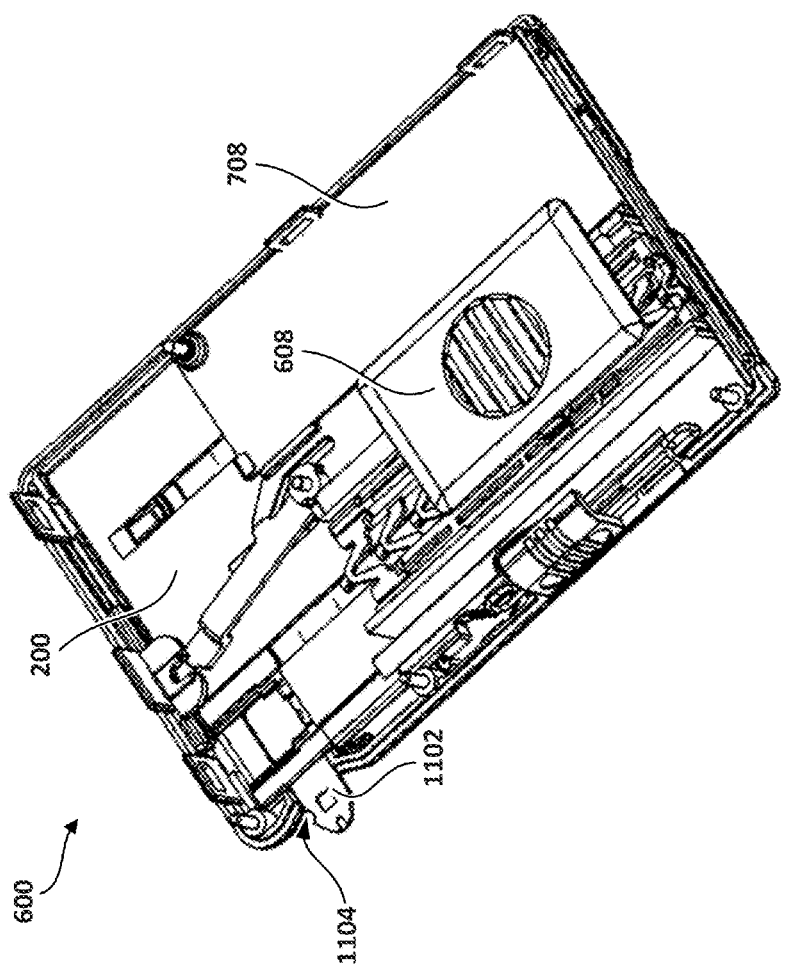
FIG. 11 shows an example metering device holding an example cartridge.

As an example, FIG. 11 shows an embodiment of metering device 600 that fully ejects a test strip 1102 through an opening 1104 in the housing of metering device 600. In particular, FIG. 11 shows metering device 600 with the top housing removed. In FIG. 11, cartridge 200 is fully inserted into metering device 600 and actuation of button 608 has caused the internal mechanisms to eject test strip 1102. Once the strip is ejected, fluid may be received into test strip 1102 and electronics 708 may test the fluids and output the results. Then, test strip 1102 may be removed from cartridge 200 and metering device 600.

Figure 12:
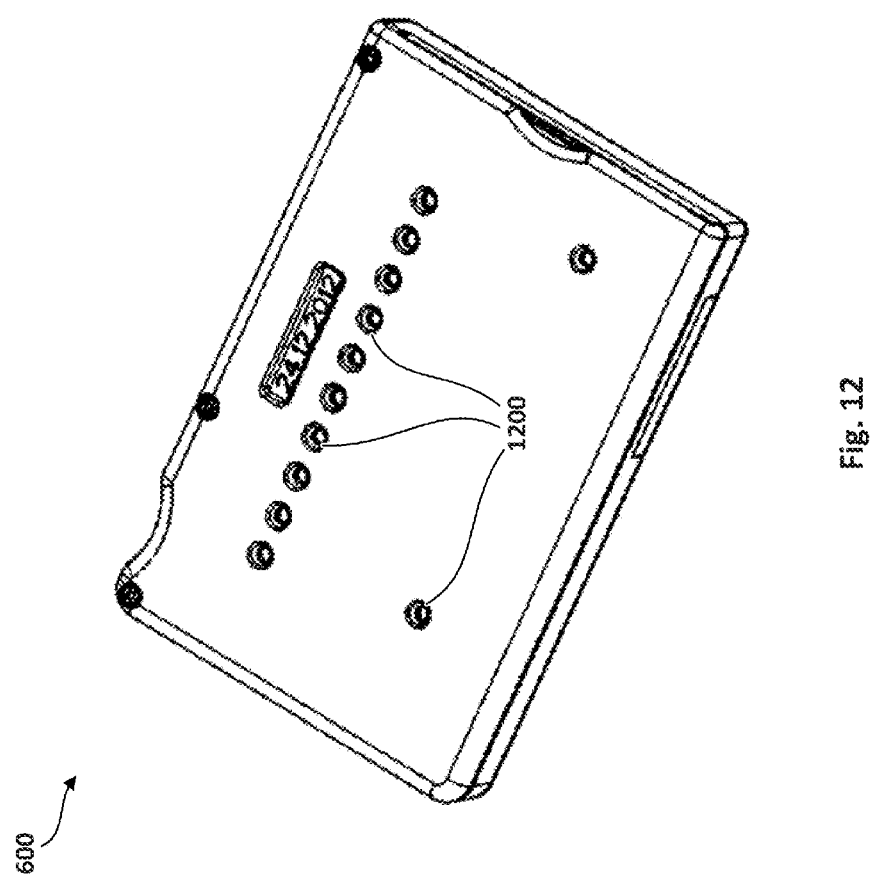
FIG. 12 shows external features of an example metering device.

As shown in FIG. 12, metering device 600 may include viewing windows 1200 for checking on the status of test strips or system. In order to monitor test strips that are inside cartridge 200, the viewing windows 1200 on metering device 600 may be lined up with corresponding viewing windows 502 (or other transparent sections) on cartridge 200. In some cases, larger portions of metering device 600 may be formed of transparent material.

Although described examples relate to uses with regard to biological fluids, a person of skill in the art would recognize that such devices could be applied to other fluids.

The construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited.

Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present disclosure. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the scope of the appended claims.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

What is claimed is:

1. A cartridge comprising:
    a first support structure configured to hold a first array of flat test-strips for fluids, wherein the first support structure is configured to hold test-strips side-by-side such that the first array has a sheet-like configuration within the first support structure;
    a thin-walled housing encompassing the first support structure;
    a mechanism configured to push a test-strip at least partially outside of the housing through an opening; and
    a first and second slider for sliding the test strips in a transport direction towards the opening;
    wherein each test strip includes a capillary tube and the cartridge includes an elastomeric sealing configured to seal the capillary tubes of the test-strips.

2. The cartridge of claim 1, further comprising a second support structure configured to hold a second array of flat test-strips, wherein the second support structure is configured to hold the second array of test-strips adjacent and parallel to the first array of flat test-strips, wherein the first array and the second array are in the same horizontal plane.

3. The cartridge of claim 2, wherein the second support structure is equivalent to the first support structure, and wherein, with respect to the first support structure, the second support structure is rotated in a flat plane by 180° around a geometric center of the cartridge.

4. The cartridge of claim 1, wherein the cartridge is sized and shaped to be roughly similar in size to a credit card.

5. The cartridge of claim 1, wherein the test-strip is removable from the cartridge.

6. The cartridge of claim 5, further comprising a second mechanism operable to move the first array of test-strips in a direction toward the opening, wherein the second mechanism is configured to move the first array of test-strips in response to the first test-strip being removed from the cartridge.

7. The cartridge of claim 1, further comprising barbs disposed in the first support structure, wherein the barbs are configured to prevent movement of the first array of test strips in a direction away from an opening in the housing.

8. The cartridge of claim 1, wherein a shape of each of the capillary tubes matches a deformed shape of the elastomeric sealing.

9. The cartridge of claim 1, wherein a rear support-area of the first support structure has a specific shape to facilitate movement of the first array of test-strips within the first support structure.

10. The cartridge of claim 1, wherein a set of external-interfacing parts are sealed against the first support structure using labyrinth seals.

11. The cartridge of claim 1, wherein a set of external-interfacing parts are sealed against the first support structure using an elastomeric material.

12. The cartridge of claim 1, further comprising viewing windows through the housing, wherein test-strips in the first array of test-strips are visible through the viewing window.

13. The cartridge of claim 2, wherein the first array of flat test-strips and the second array of flat test-strips are unused.

14. The cartridge of claim 1, wherein each test-strip includes a capillary tube having a sharpened end.

15. The cartridge of claim 2, wherein the first slider is used to move the first array of test strips and the second slider is used to move the second array of test strips.

\* \* \* \* \*